(12) United States Patent
Bacon (10) Patent No.: US 10,369,307 B2
(45) Date of Patent: *Aug. 6, 2019

(54) DISPENSER

(71) Applicant: Clinical Designs Limited, Milton Road (GB)

(72) Inventor: Raymond John Bacon, Petersfield (GB)

(*) Notice: Subject to any disclaimer, the term of this patent is extended or adjusted under 35 U.S.C. 154(b) by 362 days.

This patent is subject to a terminal disclaimer.

(21) Appl. No.: 15/420,995

(22) Filed: Jan. 31, 2017

(65) Prior Publication Data

US 2017/0151395 A1  Jun. 1, 2017

Related U.S. Application Data

(63) Continuation of application No. 11/991,680, filed as application No. PCT/GB2006/003344 on Sep. 8, 2006, now Pat. No. 9,592,355.

(30) Foreign Application Priority Data

Sep. 9, 2005 (GB) .................................. 0518400.7

(51) Int. Cl.
 *A61M 11/00* (2006.01)
 *A61M 13/00* (2006.01)
 *A61M 15/00* (2006.01)

(52) U.S. Cl.
 CPC ...... *A61M 15/0091* (2013.01); *A61M 11/006* (2014.02); *A61M 13/00* (2013.01); *A61M 15/009* (2013.01); *A61M 15/0021* (2014.02); *A61M 15/0065* (2013.01); *A61M 15/0068* (2014.02); *A61M 15/0096* (2014.02); *A61M 15/0093* (2014.02); *A61M 2202/064* (2013.01)

(58) Field of Classification Search
 CPC .......... A61M 15/0091; A61M 15/0065; A61M 11/00; A61M 11/006
 USPC ........................................ 128/200.14–200.23
 See application file for complete search history.

(56) References Cited

U.S. PATENT DOCUMENTS

| | | |
|---|---|---|
| 721,964 A | 3/1903 | Miller |
| 2,002,835 A | 5/1935 | Rose |
| 2,716,013 A | 11/1948 | Tinker |
| 2,922,613 A | 1/1960 | Beacham et al. |
| 3,103,335 A | 9/1963 | Martinez |
| 3,190,497 A | 6/1965 | Anthon |
| 3,329,389 A | 7/1967 | Clark |
| 3,506,004 A | 4/1970 | Mann et al. |
| 3,598,288 A | 8/1971 | Posgate |
| 3,636,949 A | 1/1972 | Kropp |
| 3,927,484 A | 12/1975 | Spiegel et al. |
| 4,142,651 A | 3/1979 | Leopoldi et al. |

(Continued)

FOREIGN PATENT DOCUMENTS

| | | |
|---|---|---|
| AU | 776816 | 7/2002 |
| AU | 2003234746 | 9/2003 |

(Continued)

*Primary Examiner* — Kristen Matter (74) *Attorney, Agent, or Firm* — Lambert Shortell & Connaughton; Gary E. Lambert; David J. Connaughton, Jr.

(57) ABSTRACT

A medicated inhalant dispenser has a plastics material body having a mouthpiece. A pressurized, inhalant source has a canister and a sprout which his moved towards the canister for release of a dose from the canister. The sprout is accommodated in a junction member, which is movable by a cam connected to a pivotal cover for the mouthpiece.

22 Claims, 6 Drawing Sheets

(56) References Cited

U.S. PATENT DOCUMENTS

| | | |
|---|---|---|
| 4,361,148 A | 11/1982 | Shackleford et al. |
| 4,576,157 A | 3/1986 | Raghuprasad |
| 4,664,107 A | 5/1987 | Wass et al. |
| 4,753,371 A | 6/1988 | Michielin et al. |
| 4,817,822 A | 4/1989 | Rand et al. |
| 5,020,527 A | 6/1991 | Dessertine |
| 5,031,610 A | 7/1991 | Armstrong et al. |
| 5,069,204 A | 12/1991 | Smith et al. |
| 5,119,806 A | 6/1992 | Palson et al. |
| 5,217,004 A | 6/1993 | Blasnik et al. |
| 5,261,601 A | 11/1993 | Ross et al. |
| 5,273,172 A | 12/1993 | Rossbach et al. |
| 5,408,994 A | 4/1995 | Wass et al. |
| 5,421,482 A | 6/1995 | Garby et al. |
| 5,487,378 A | 1/1996 | Robertson et al. |
| 5,501,375 A | 3/1996 | Nilson |
| 5,511,540 A | 4/1996 | Bryant et al. |
| 5,549,226 A | 8/1996 | Kopp |
| 5,611,444 A | 3/1997 | Garby et al. |
| 5,623,920 A | 4/1997 | Bryant |
| 5,682,875 A | 11/1997 | Blower et al. |
| 5,718,355 A | 2/1998 | Garby et al. |
| 5,772,085 A | 6/1998 | Bryant et al. |
| 5,857,275 A | 1/1999 | Deal et al. |
| 5,904,139 A | 5/1999 | Hauser et al. |
| 5,988,496 A | 11/1999 | Bruna |
| 5,996,577 A | 12/1999 | Ohki et al. |
| 6,032,835 A | 3/2000 | Burt et al. |
| 6,085,742 A | 7/2000 | Wachter et al. |
| 6,149,054 A | 11/2000 | Cirrillo et al. |
| 6,164,494 A | 12/2000 | Marelli |
| 6,182,655 B1 | 2/2001 | Keller et al. |
| 6,234,168 B1 | 5/2001 | Bruna |
| 6,240,918 B1 | 6/2001 | Ambrosio et al. |
| 6,253,762 B1 | 7/2001 | Britto |
| 6,260,549 B1 | 7/2001 | Sosiak |
| 6,283,365 B1 | 9/2001 | Bason |
| 6,309,623 B1 | 10/2001 | Weers et al. |
| 6,318,361 B1 | 11/2001 | Sosiak |
| 6,325,062 B1 | 12/2001 | Sosiak |
| 6,354,290 B1 | 3/2002 | Howlett |
| 6,397,839 B1 | 6/2002 | Stradella |
| 6,405,727 B1 | 6/2002 | MacMichael et al. |
| 6,422,234 B1 | 7/2002 | Bacon |
| 6,425,392 B1 | 7/2002 | Sosiak |
| 6,427,683 B1 | 8/2002 | Drachmann et al. |
| 6,431,168 B1 | 8/2002 | Rand et al. |
| 6,439,227 B1 | 8/2002 | Myrman et al. |
| 6,443,146 B1 | 9/2002 | Voges |
| 6,460,537 B1 | 10/2002 | Bryant et al. |
| 6,510,847 B1 | 1/2003 | Helgesson et al. |
| 6,516,799 B1 | 2/2003 | Greenwood et al. |
| 6,546,928 B1 | 4/2003 | Ashurst et al. |
| 6,553,988 B1 | 4/2003 | Holroyd |
| 6,601,582 B2 | 8/2003 | Rand et al. |
| 6,615,827 B2 | 9/2003 | Greenwood et al. |
| 6,655,371 B2 | 12/2003 | Gallops, Jr. |
| 6,655,379 B2 | 12/2003 | Clark et al. |
| 6,659,307 B1 | 12/2003 | Stradella |
| 6,745,761 B2 | 5/2004 | Christrup et al. |
| 6,752,153 B1 | 6/2004 | Eckert |
| 6,755,190 B2 | 6/2004 | Rasmussen |
| 6,766,220 B2 | 7/2004 | McRae et al. |
| 6,823,863 B2 | 11/2004 | Huxham et al. |
| 6,860,262 B2 | 3/2005 | Christrup et al. |
| 6,866,037 B1 | 3/2005 | Aslin et al. |
| 6,866,038 B2 | 3/2005 | Bacon |
| 6,907,876 B1 | 6/2005 | Clark et al. |
| 6,926,002 B2 | 8/2005 | Scarrott et al. |
| 7,007,689 B2 | 3/2006 | Burns |
| 7,036,505 B2 | 5/2006 | Bacon et al. |
| 7,047,964 B2 | 5/2006 | Bacon |
| 7,047,967 B2 | 5/2006 | Knudsen |
| 7,072,738 B2 | 7/2006 | Bonney et al. |
| 7,093,594 B2 | 8/2006 | Harrison et al. |
| 7,100,530 B2 | 9/2006 | Lu |
| 7,107,986 B2 | 9/2006 | Rand et al. |
| 7,107,988 B2 | 9/2006 | Pinon et al. |
| 7,131,441 B1 | 11/2006 | Keller et al. |
| 7,147,170 B2 | 12/2006 | Nguyen et al. |
| 7,167,776 B2 | 1/2007 | Maharajh et al. |
| 7,191,918 B2 | 3/2007 | Ouyang et al. |
| 7,195,134 B2 | 3/2007 | Ouyang et al. |
| 7,225,805 B2 | 6/2007 | Bacon |
| 7,234,460 B2 | 6/2007 | Greenleaf et al. |
| 7,237,727 B2 | 7/2007 | Wang |
| 7,270,124 B2 | 9/2007 | Rasmussen |
| 7,275,660 B2 | 10/2007 | Stradella et al. |
| 7,296,567 B2 | 11/2007 | Mahon et al. |
| 7,299,800 B2 | 11/2007 | Stradella |
| 7,299,801 B2 | 11/2007 | Hodson |
| 7,306,116 B2 | 12/2007 | Fuchs |
| 7,318,434 B2 | 1/2008 | Gumaste et al. |
| 7,322,352 B2 | 1/2008 | Minshull et al. |
| 7,331,340 B2 | 2/2008 | Barney |
| 7,334,577 B2 | 2/2008 | Gumaste et al. |
| 7,341,057 B2 | 3/2008 | Scarrott et al. |
| 7,347,200 B2 | 3/2008 | Jones et al. |
| 7,347,202 B2 | 3/2008 | Aslin et al. |
| 7,387,121 B2 | 6/2008 | Harvey |
| 7,400,940 B2 | 7/2008 | McRae et al. |
| 7,418,961 B2 | 9/2008 | Jones et al. |
| 7,448,342 B2 | 11/2008 | von Schuckmann |
| 7,454,267 B2 | 11/2008 | Bonney et al. |
| 7,497,214 B2 | 3/2009 | Hodson |
| 7,510,100 B2 | 3/2009 | Stradella et al. |
| 7,597,099 B2 | 10/2009 | Jones et al. |
| 7,637,260 B2 | 12/2009 | Holroyd |
| 7,720,124 B2 | 5/2010 | Rasmussen |
| 7,721,731 B2 | 5/2010 | Bacon |
| 7,814,900 B2 | 10/2010 | Bacon |
| 7,854,226 B2 | 12/2010 | Pinon et al. |
| 7,950,389 B2 | 5/2011 | Eason et al. |
| 2001/0013342 A1 | 8/2001 | Burns |
| 2001/0013343 A1 | 8/2001 | Andersson |
| 2001/0025639 A1 | 10/2001 | Christrup et al. |
| 2002/0011247 A1 | 1/2002 | Ivri et al. |
| 2002/0088458 A1 | 7/2002 | Christrup et al. |
| 2002/0100473 A1 | 8/2002 | Christrup et al. |
| 2002/0104530 A1 | 8/2002 | Ivri et al. |
| 2002/0104532 A1 | 8/2002 | Christrup et al. |
| 2002/0189611 A1 | 12/2002 | Greenwood et al. |
| 2003/0089368 A1 | 5/2003 | Zhao |
| 2003/0106550 A1 | 6/2003 | Harvey |
| 2003/0116155 A1 | 6/2003 | Rasmussen |
| 2003/0136401 A1 | 7/2003 | Jansen |
| 2003/0138559 A1 | 7/2003 | Ashurst et al. |
| 2003/0150448 A1 | 8/2003 | Bacon |
| 2003/0178021 A1 | 9/2003 | Rasmussen |
| 2003/0183225 A1 | 10/2003 | Knudsen |
| 2003/0230305 A1 | 12/2003 | Christrup et al. |
| 2004/0020486 A1 | 2/2004 | Huxham et al. |
| 2004/0025867 A1 | 2/2004 | Holroyd |
| 2004/0025868 A1 | 2/2004 | Bruna |
| 2004/0025870 A1 | 2/2004 | Harrison |
| 2004/0055596 A1 | 3/2004 | Bacon |
| 2004/0065320 A1 | 4/2004 | Bacon |
| 2004/0065326 A1 | 4/2004 | MacMichael et al. |
| 2004/0069301 A1 | 4/2004 | Bacon |
| 2004/0079361 A1 | 4/2004 | Clayton et al. |
| 2004/0079362 A1 | 4/2004 | Christrup et al. |
| 2004/0089299 A1 | 5/2004 | Bonney et al. |
| 2004/0107962 A1 | 6/2004 | Harrison et al. |
| 2004/0134488 A1 | 7/2004 | Davies |
| 2004/0134489 A1 | 7/2004 | Burns |
| 2004/0139965 A1 | 7/2004 | Greenleaf et al. |
| 2004/0139966 A1 | 7/2004 | Hodson |
| 2004/0144798 A1 | 7/2004 | Ouyang et al. |
| 2004/0187865 A1 | 9/2004 | Ashurst et al. |
| 2005/0016528 A1 | 1/2005 | Aslin et al. |
| 2005/0076904 A1 | 4/2005 | Jones et al. |
| 2005/0081846 A1 | 4/2005 | Barney |
| 2005/0087191 A1 | 4/2005 | Morton et al. |
| 2005/0126469 A1 | 6/2005 | Lu |

(56) References Cited

U.S. PATENT DOCUMENTS

| | | |
|---|---|---|
| 2005/0143866 A1 | 6/2005 | McRae et al. |
| 2005/0205512 A1 | 9/2005 | Scarrott et al. |
| 2005/0209558 A1 | 9/2005 | Marx |
| 2005/0263612 A1 | 12/2005 | Wang |
| 2006/0011197 A1 | 1/2006 | Hodson |
| 2006/0032971 A1 | 2/2006 | Baldwin |
| 2006/0037611 A1 | 2/2006 | Mahon et al. |
| 2006/0060192 A1 | 3/2006 | Lu et al. |
| 2006/0071027 A1 | 4/2006 | Davies et al. |
| 2006/0131346 A1 | 6/2006 | Purkins et al. |
| 2006/0150971 A1 | 7/2006 | Lee et al. |
| 2006/0151524 A1 | 7/2006 | Stradella et al. |
| 2006/0163275 A1 | 7/2006 | Stradella et al. |
| 2006/0174869 A1 | 8/2006 | Gumaste et al. |
| 2006/0186223 A1 | 8/2006 | Wang |
| 2006/0231093 A1 | 10/2006 | Burge et al. |
| 2006/0237002 A1 | 10/2006 | Bonney et al. |
| 2006/0237009 A1 | 10/2006 | Jones et al. |
| 2006/0254581 A1 | 11/2006 | Genova et al. |
| 2006/0278225 A1 | 12/2006 | MacMichael et al. |
| 2006/0283444 A1 | 12/2006 | Jones et al. |
| 2006/0289005 A1 | 12/2006 | Jones et al. |
| 2007/0017511 A1 | 1/2007 | Ohki et al. |
| 2007/0029341 A1 | 2/2007 | Stradella et al. |
| 2007/0051745 A1 | 3/2007 | Poulard |
| 2007/0056502 A1 | 3/2007 | Lu |
| 2007/0056580 A1 | 3/2007 | Jones et al. |
| 2007/0056585 A1 | 3/2007 | Davies et al. |
| 2007/0062518 A1 | 3/2007 | Geser et al. |
| 2007/0062522 A1 | 3/2007 | Bacon |
| 2007/0089735 A1 | 4/2007 | Langford et al. |
| 2007/0119450 A1 | 5/2007 | Wharton et al. |
| 2007/0144514 A1 | 6/2007 | Yeates et al. |
| 2007/0163576 A1 | 7/2007 | Bacon |
| 2007/0181120 A1 | 8/2007 | Wright et al. |
| 2007/0181123 A1 | 8/2007 | Houzego |
| 2007/0194041 A1 | 8/2007 | Stradella et al. |
| 2007/0210102 A1 | 9/2007 | Stradella et al. |
| 2007/0241136 A1 | 10/2007 | Poulard |
| 2007/0246042 A1 | 10/2007 | Purkins et al. |
| 2007/0251950 A1 | 11/2007 | Bacon |
| 2007/0284383 A1 | 12/2007 | Wright et al. |
| 2008/0017189 A1 | 1/2008 | Ruckdeschel et al. |
| 2008/0017193 A1 | 1/2008 | Jones et al. |
| 2008/0035144 A1 | 2/2008 | Bowman et al. |
| 2008/0041877 A1 | 2/2008 | Stradella et al. |
| 2008/0047556 A1 | 2/2008 | Hodson |
| 2008/0060643 A1 | 3/2008 | Hodson et al. |
| 2008/0066742 A1 | 3/2008 | Hodson et al. |
| 2008/0115784 A1 | 5/2008 | Gumaste et al. |
| 2008/0135575 A1 | 6/2008 | Ingram et al. |
| 2008/0135576 A1 | 6/2008 | Bacon |
| 2008/0210224 A1 | 9/2008 | Brunnberg et al. |
| 2008/0210226 A1 | 9/2008 | Butterworth et al. |
| 2008/0251004 A1 | 10/2008 | Stradella et al. |
| 2008/0283541 A1 | 11/2008 | Warby et al. |
| 2008/0314383 A1 | 12/2008 | Barney et al. |
| 2009/0114219 A1 | 5/2009 | Ferris et al. |
| 2009/0229604 A1 | 9/2009 | Pearson et al. |
| 2009/0229607 A1 | 9/2009 | Brunnberg |
| 2009/0293870 A1 | 12/2009 | Brunnberg et al. |
| 2009/0308385 A1 | 12/2009 | Brewer |
| 2010/0012115 A1 | 1/2010 | Bacon |
| 2010/0065050 A1 | 3/2010 | Holroyd |

FOREIGN PATENT DOCUMENTS

| | | |
|---|---|---|
| AU | 2003234748 | 9/2003 |
| AU | 2003260340 B2 | 4/2004 |
| AU | 2003260340 C1 | 4/2004 |
| DE | 629163 | 4/1936 |
| DE | 1077932 | 3/1960 |
| DE | 10061723 | 5/1973 |
| DE | 8715223 | 2/1988 |
| DE | 4105939 | 8/1992 |
| DE | 4111895 | 10/1992 |
| DE | 29511334 | 11/1995 |
| DE | 19745513 | 4/1999 |
| DE | 29818662 | 4/2000 |
| DE | 202004021188 | 4/2007 |
| EP | 0414536 | 2/1991 |
| EP | 0501365 | 2/1992 |
| EP | 0476991 | 3/1992 |
| EP | 0490797 | 6/1992 |
| EP | 0516510 | 12/1992 |
| EP | 0428380 | 10/1993 |
| EP | 0563120 | 10/1993 |
| EP | 0629563 | 12/1994 |
| EP | 0632734 | 1/1995 |
| EP | 0650452 | 5/1995 |
| EP | 0682539 | 11/1995 |
| EP | 0883415 B | 12/1998 |
| EP | 0984805 | 3/2000 |
| EP | 1003583 | 5/2000 |
| EP | 1008361 | 6/2000 |
| EP | 1019125 | 7/2000 |
| EP | 1059952 | 12/2000 |
| EP | 1131122 | 9/2001 |
| EP | 1229953 | 8/2002 |
| EP | 1443997 | 10/2002 |
| EP | 1267970 | 1/2003 |
| EP | 1267973 | 1/2003 |
| EP | 1267974 | 1/2003 |
| EP | 1267975 | 1/2003 |
| EP | 1289589 | 3/2003 |
| EP | 1298065 | 4/2003 |
| EP | 1320395 | 6/2003 |
| EP | 2002034319 | 7/2003 |
| EP | 1357966 | 11/2003 |
| EP | 1443997 | 8/2004 |
| EP | 1019125 B1 | 11/2005 |
| EP | 1632210 | 3/2006 |
| EP | 1229953 B1 | 11/2006 |
| EP | 1833541 | 9/2007 |
| FR | 2654627 | 5/1991 |
| FR | 2660630 | 10/1991 |
| FR | 2701653 | 8/1994 |
| FR | 2775668 | 9/1999 |
| GB | 161969 | 7/1922 |
| GB | 939324 | 10/1963 |
| GB | 1270272 | 4/1969 |
| GB | 2429166 | 1/1971 |
| GB | 1288971 | 9/1972 |
| GB | 2262452 | 6/1993 |
| GB | 2262454 A | 6/1993 |
| GB | 2263076 | 7/1993 |
| GB | 2263873 | 8/1993 |
| GB | 2264238 | 8/1993 |
| GB | 2264238 A | 8/1993 |
| GB | 2266466 | 11/1993 |
| GB | 2279571 | 1/1995 |
| GB | 2279879 | 1/1995 |
| GB | 2292891 | 3/1996 |
| GB | 2337040 | 11/1999 |
| GB | 2344534 | 6/2000 |
| GB | 2360219 | 9/2001 |
| GB | 2366519 B | 11/2002 |
| GB | 2398250 | 8/2004 |
| GB | 2398250 A | 8/2004 |
| GB | 2398251 | 8/2004 |
| GB | 2398252 | 8/2004 |
| GB | 2414187 | 11/2005 |
| GB | 2398251 A | 8/2007 |
| WO | 9010469 | 9/1990 |
| WO | 9013335 | 11/1990 |
| WO | 9200770 | 1/1992 |
| WO | 9207599 | 5/1992 |
| WO | 9207600 | 5/1992 |
| WO | 9208509 | 5/1992 |
| WO | 9218188 | 10/1992 |
| WO | 9303783 | 3/1993 |
| WO | 9312831 | 7/1993 |
| WO | 9324167 | 12/1993 |
| WO | 9404209 | 3/1994 |

(56) References Cited

FOREIGN PATENT DOCUMENTS

| | | |
|---|---|---|
| WO | 9405359 | 3/1994 |
| WO | 9419040 | 9/1994 |
| WO | 9419042 | 9/1994 |
| WO | 9508484 | 3/1995 |
| WO | 9511715 | 5/1995 |
| WO | 9639337 | 12/1996 |
| WO | 9711296 | 3/1997 |
| WO | WO199841254 | 9/1998 |
| WO | 9936116 | 7/1999 |
| WO | 9957019 | 11/1999 |
| WO | 9965551 | 12/1999 |
| WO | 0016838 | 3/2000 |
| WO | 0050111 | 8/2000 |
| WO | 0078378 | 12/2000 |
| WO | 0132247 | 5/2001 |
| WO | 0141849 | 6/2001 |
| WO | 0170319 | 9/2001 |
| WO | 0211802 | 2/2002 |
| WO | WO200211802 | 2/2002 |
| WO | 0224265 | 3/2002 |
| WO | 0238207 | 5/2002 |
| WO | 0245783 | 6/2002 |
| WO | 02043794 | 6/2002 |
| WO | 02056949 | 7/2002 |
| WO | 02058771 | 8/2002 |
| WO | 02078595 | 10/2002 |
| WO | 02100468 | 12/2002 |
| WO | 02100469 | 12/2002 |
| WO | 03012565 | 2/2003 |
| WO | 2002002167 | 4/2003 |
| WO | 036190 | 7/2003 |
| WO | 03080161 | 10/2003 |
| WO | 04001664 | 12/2003 |
| WO | 2004022242 | 3/2004 |
| WO | 2004026380 | 4/2004 |
| WO | 2004028608 | 4/2004 |
| WO | 2004041339 | 5/2004 |
| WO | 2004071562 | 8/2004 |
| WO | 2004071563 | 8/2004 |
| WO | 2004071564 | 8/2004 |
| WO | 2004078236 | 9/2004 |
| WO | 2004089451 | 10/2004 |
| WO | 2004096329 | 11/2004 |
| WO | 2005034833 | 4/2005 |
| WO | 2005081833 | 9/2005 |
| WO | 2005114563 | 12/2005 |
| WO | 2006028843 | 3/2006 |
| WO | WO 2006/054083 A1 | 5/2006 |
| WO | 06062449 | 6/2006 |
| WO | 2006062449 | 6/2006 |
| WO | WO2006110080 | 10/2006 |
| WO | 06119766 | 11/2006 |
| WO | 2006115732 | 11/2006 |
| WO | 2006119766 | 11/2006 |
| WO | 200712854 | 2/2007 |
| WO | 2007015665 | 2/2007 |
| WO | 2007029019 | 3/2007 |
| WO | 2007066140 | 6/2007 |
| WO | 2007076064 | 7/2007 |
| WO | 2007077450 | 7/2007 |
| WO | 07141520 | 12/2007 |
| WO | 2007141520 | 12/2007 |
| WO | 2008012456 | 1/2008 |
| WO | 2008025087 | 3/2008 |
| WO | 2008030837 | 3/2008 |
| WO | 2008040772 | 4/2008 |
| WO | 200807936 | 7/2008 |
| WO | 2008079350 | 7/2008 |
| WO | 2008087369 | 7/2008 |
| WO | 2008104366 | 9/2008 |
| WO | 2008119552 | 10/2008 |
| WO | 2008148864 | 12/2008 |

DISPENSER

BACKGROUND OF THE INVENTION

Field of the Invention

The present invention relates to a dispenser, particularly though not exclusively for dispensing aerosol or powder borne medicaments.

Description of the Related Art

In my prior International Patent Application, PCT/GB98/00770, at least as amended on entry in the European Regional Phase, there is described and claimed:

A dispenser for a gaseous, gas borne or droplet substance, the dispenser including:
- a body having a mouthpiece with an inhalation/insufflation orifice at its end;
- a junction in the body for a source of gas or evaporable liquid comprising or containing the said substance (the source being carried by the body); and
- a breath actuatable valve, for controlling the release of said gas or liquid, comprising:
- a valve inlet connected to the junction;
- a valve outlet;
- a flexible tube extending from the junction, between the inlet and the outlet, for receiving the said gas or liquid, the tube having a portion which is movable between a closed position in which the tube is kinked for closure of the valve and an open position in which the tube is un-kinked for opening of the valve; and
- a movable member, for moving the movable portion of the tube to control its kinking, and being movably mounted in the body for movement by the act of inhalation from a rest position towards the orifice—or at least in the direction of air flow through the dispenser;
- the tube being kinked to an obturating extent when the movable member is in a rest position and un-kinked when the movable member is moved on inhalation for release of the gas or liquid.

Such a dispenser can loosely be classed as a breath actuated, kink valve dispenser and is referred to herein as "My Earlier Breath Actuated, Kink Valve Dispenser".

The main embodiments of My Earlier Breath Actuated, Kink Valve Dispenser included a piston acted on by a differential breath induced pressure. The resultant, force generated is generally sufficient to operate the dispenser by drawing the piston towards the dispenser's mouthpiece and extending and opening the kink valve. Nevertheless, I felt that the dispenser is susceptible of improvement. In particular, in my British Patent Application published under No. 2,381,461 on 7 May 2003, 1 described and claimed: a dispenser for a gaseous, gas borne or droplet substance contained in a source thereof, the dispenser including:
- a body with a mouthpiece;
- a junction member in the body for the substance source; and
- a breath actuatable valve, for controlling the release of the gas or liquid containing or comprising the substance, the valve comprising:
- a flexible tube for receiving the said gas or liquid, the tube extending from a valve inlet connected to the junction member and having a portion which is kinkable for closure of the valve and movable to an open position in Which the tube is un-kinked for opening of the valve; and
- a member arranged for movement in the body by inhalation to un-kink the valve;
- the tube being kinked to an obturating extent when the movable member is in a ready position and un-kinked when the movable member is moved on inhalation for release of the gas or liquid; wherein:
- the movable member is or includes a flap arranged in the body for action of breath on it on inhalation;
- the junction member, the flexible tube and the movable flap are a single injection moulding of plastics material; and
- the movable flap is pivotally connected to the junction member.

This dispenser is referred to herein as "My First Production Breath Actuated, Kink Valve Dispenser". It is proving successful, particularly in combination with the "Unification Feature" of the dispenser described in and claimed in my British Patent Application published under No. 2,401,321 on 10 Nov. 2004, namely that of a dispenser for a gaseous, gas borne or droplet substance contained in a source thereof, the dispenser comprising:
- a substance source having:
- an external surface devoid of any feature intended for longitudinal location of the source and
- a spout displaceable inwards of the source to a dispense position for dispensing a substance dose from the source;
- a body having:
- a mouthpiece via which the substance dose can be inhaled and
- a socket sized for lateral location of the source via its external surface, but devoid of any body feature intended for longitudinal location thereof;
- a junction member for the spout, the junction member being arranged in the body to be slidable to a set position for displacing the spout to its dispense position;
- an action for slidably loving the junction member to the set position; and
- a unification of the source or a source locator to the body for locating the source longitudinally with the spout in its dispense position when the junction member is in its set position, the locator where provided extending from the body, outside the source and at least partially across the end of the source to provide a longitudinal location for the source, locating it when the movable junction member acts to depress the spout inwards of the source.

The unification enables tolerances in the source, particular its overall length from the end of the spout to the opposite end of its container, to be taken account of.

SUMMARY OF THE INVENTION

The object of the present invention is to provide an alternative means of taking account of the variation in the length of the container and relies on the inventive concept of measuring the position of the opposite end of the container and adjusting its abutment in the dispenser or the position of a member providing such abutment individually for each dispenser or indeed in a carrier for the container of the source.

According to a first aspect of the invention, there is provided an enclosed aerosol source comprising an assembled combination of the aerosol source combination as such and an enclosure:
- the aerosol source having:
- a canister,
- a spout at one end of the canister, the spout being movable inwards of the canister for substance release, a spring urging the spout outwards of the canister with a force required to be overcome for release movement inwards, and a valve for releasing a substance from the canister on longitudinal movement of the spout against the spring; and the enclosure having:

at least one dispense-mechanism, positioning feature at a determined position; and an adjustable location for the canister, the location being adjusted to provide a determined position of the spout with respect to the dispense-mechanism, positioning feature, when the aerosol canister has been assembled into the enclosure, the arrangement being such that on movement of the spout through determined stroke with respect to the dispense-mechanism, positioning feature and against the spring substance release is predictable.

Normally the enclosed aerosol will be for use inhalation or insufflation of medicament.

Preferably, the dispense-mechanism, positioning feature is an abutment feature for a body including:

a mouthpiece for inhalation/insufflation of the substance, a movable junction for receiving the spout and a dose release mechanism able to be cocked to move the junction and receive a substance dose and to be triggered by inhalation releasing a substance dose and an abutment feature for abutment of the enclosure abutment feature;

the two abutment features being connected together.

Alternatively, the enclosure can include a mechanism for moving the canister towards the junction, the adjustable location being between the mechanism and the canister or between the mechanism and the enclosure and in which case:

the dispense-mechanism, positioning feature is an abutment feature for a body including:

a mouthpiece for inhalation/insufflation of the substance and a movable junction for receiving the spout and an abutment feature for abutment of the enclosure abutment feature;

the two abutment features being connected together.

In either case, the two abutment features can be connected together either by interengagement of complementary features or by a welded joint or by an adhesive joint.

In another alternative, the dispense-mechanism, positioning feature is a counter actuation feature, the enclosure including:

an outer sleeve, having the counter actuation feature:

an inner sleeve, within the outer sleeve and without the canister;

an inner counter actuation feature on the inner sleeve complementary with outer sleeve feature, the features being adapted to index the sleeves with aerosol actuation;

means for indicating indexation as a counter of aerosol actuation.

The adjustable location can take a variety of different forms, for instance:

a compressible end location for the canister in the enclosure, or a part added to the enclosure, typically a washer of aluminium honeycomb material, or a deformable part of the enclosure, or an integrally moulded honey comb or set of radial ribs, or a rigid disc or washer pressed into the deformable part of the enclosure, or a sleeve surrounding the canister, in which case, the sleeve can be a portion of the enclosure in which the canister is an interference fit or the sleeve can be a series of ribs radiating inwards from the enclosure to the canister, or an adhesive between the canister and a sleeve of the enclosure surrounding the canister.

The enclosure will normally be imperforate at the end of the canister opposite from the spout and along the side thereof although the enclosure can be skeletal.

According to another aspect of the invention, there is provided an adjustment method, in the combining of an aerosol source and an enclosure of the first aspect of the invention, the method consisting in the steps of:

measuring the overall length of the source from the distal end of its spout to its other end;

adjusting the adjustable location.

Where the adjustable location is a compressible end location for the canister in the enclosure:

the measurement step consists of measurement of the length of the source, and the adjustment step consists of the adjusting the compressible end location to a standard dimension less the length of the source, the standard dimension being the distance from a support for the compressible location and the dispense-mechanism, positioning feature and a fixed use dimension from the dispense-mechanism, positioning feature to the end of the spout.

Whilst the overall length of the source can be measured, the measurement step can consist of indirectly measuring the length of the source by measuring the position of the end of the source with respect to a datum in the body, with the source and the spout held towards the junction with no end float, the location then being adjusted to provide a determined position of the end of the source in comparison with the dispense-mechanism, positioning feature.

The adjustable location can be adjusted by a variety of means, for instance, by:

machining, or by crushing with a force controlled to be a determined amount higher than the dose release force of the source, in which case the crush force is preferably substantially double the release force, or by urging one portion of the adjustable location which is a tight fit on another portion to an adjusted position, or by plastic deformation of the adjustable location.

The adjustable location can be an interference fit of a sleeve in the enclosure with the side of the canister, and in which case:

the measurement step consists of measurement of the length of the source, and the adjustment step consists of the adjusting the longitudinal position of the canister in the enclosure to a fixed used dimension from the dispense-mechanism, positioning feature to the end of the spout, the canister remaining in position due to interference between the sleeve and the canister.

Alternatively, the adjustable location can include an adhesive between the canister and a sleeve of the enclosure surrounding the canister, and in which case:

the measurement step consists of measurement of the length of the source, and the adjustment step consists of the adjusting the longitudinal position of the canister in the enclosure to a fixed used dimension from the dispense-mechanism, positioning feature to the end of the spout and setting/ allowing to set the adhesive, the canister remaining in position due to the adhesive between the sleeve and the canister.

Again the measurement step can be made with the dose release mechanism in its state for moving the spout for release of a dose from the source and the source urged towards the junction for such release and the adjustment being compensated for stroke of the junction and the spout.

Alternatively the measurement step can be made with the spout in its quiescent position with respect to the source and the junction and the release mechanism being in their normal rest position state from which they are moved for dose release.

Preferably, the adjustment of the adjustable location is such that the canister is supported with negligible end float.

BRIEF DESCRIPTION OF THE DRAWINGS

To help understanding of the invention, a specific embodiment thereof will now be described by way of example and with reference to the accompanying drawings, in which.

DETAILED DESCRIPTION OF THE PREFERRED EMBODIMENT

Referring first to FIGS. 1 to 8, a medicated inhalant dispenser 1 has a plastics material body 2 having a mouthpiece 3. A pressurised, metered dose, inhalant source 4 has an aluminium canister 5 and a spout 6, which is moved towards the canister for release of a dispensing or a dose from the canister. The spout is accommodated in a junction member 7, which is movable by a cam 8 connected to a pivotal cover 9 for the mouthpiece. Opening of the cover sets a breath actuable kink valve 10, having a nozzle 11 through which the inhalant is released and a breath flap 12 actuation. Opening also causes the junction member to be lifted for dose dispensing into the kink valve. Breathing in releases the dose for inhalation.

This operation is described in more detail in my British Patent Application published under No. 2,381,461 on My First Production Breath Actuated, Kink Valve Dispenser.

In that dispenser, the source was pinned in the body at a crimp 13. However, this can cause reliability issues in the stack up of tolerances. The Unification feature addressed these issues.

Figures 1, 2:
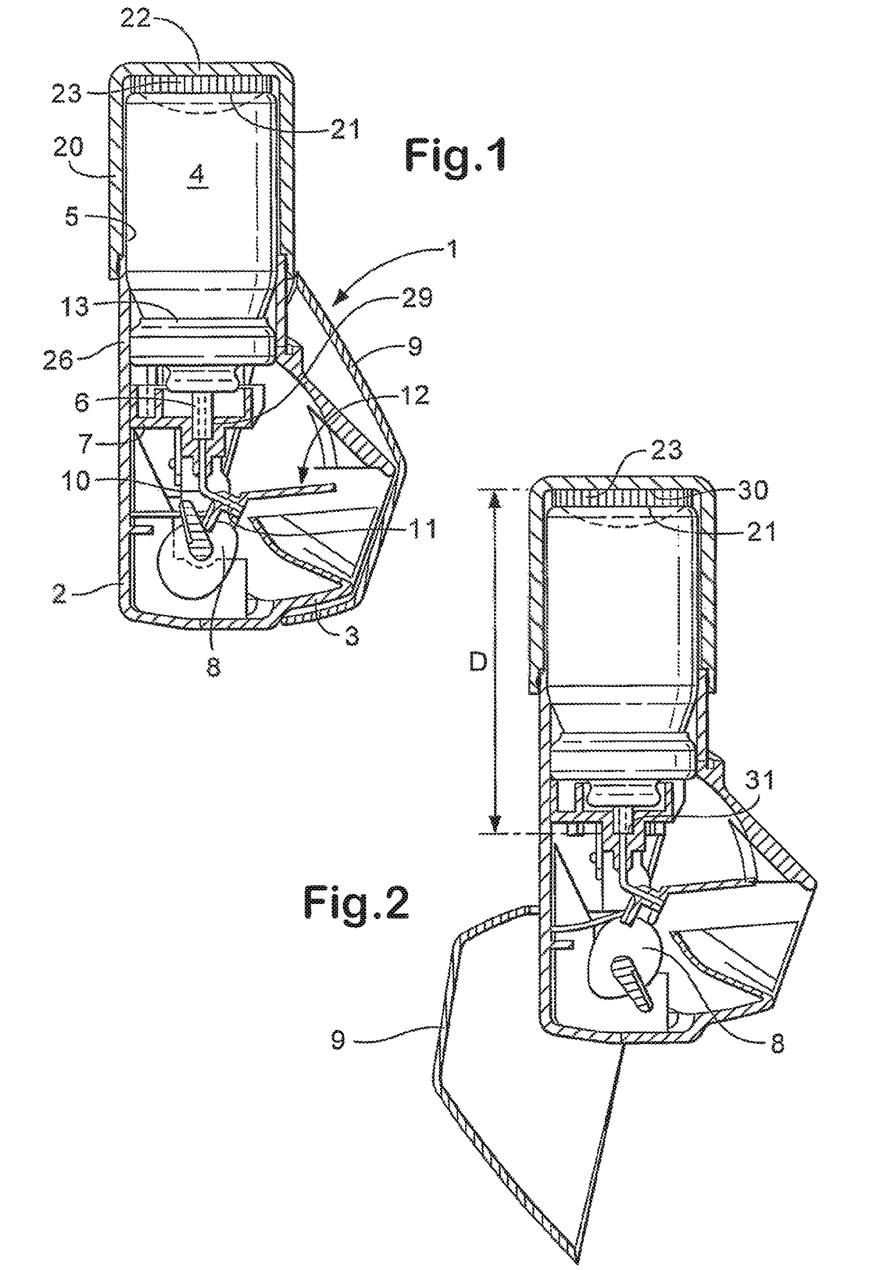
FIG. 1 is a cross-sectional side view of a dispenser similar to My First Production Breath Actuated, Kink Valve Dispenser, but improved in accordance with the present invention, the dispenser being shown in its quiescent state.
FIG. 2 is a similar view of the dispenser of FIG. 1 in its state having just dispensed a dose.

In the dispenser of the present invention, a closed sleeve 20 is provided for abutment of the end 21 of the canister as the junction member is moved towards the canister. Between the canister end 21 and an end 22 of the closed sleeve, an adjustable abutment 23 is provided. The dosed sleeve is located on the body by contact of a dispense-mechanism, positioning step 24 in its orifice with an end surface 25 of a source receptacle 26 of the body of the dispensing mechanism. At a skirt 27 of the closed sleeve, the latter is laser welded L to the receptacle 26, i.e. to the body 2, at an end portion 28 of the receptacle 26. This arrangement provides that the closed sleeve is positioned on the body with well toleranced dimensions. Thus the dimension D between the bottom of a bore 29 in the junction member 7 and abutment face 30 of the closed end 22, whether the junction member is in its quiescent position shown in FIG. 1 or its advanced dose dispensing position shown in Figure is closely predictable.

However, due to its structure involving compressed, elastomeric members (not shown) and the crimp closure 12 of the source, the overall length of the source from distal end 31 of the spout to the opposite canister end 21 is not predictable with the same degree of certainty. Accordingly reliable operation cannot be predicted with sufficient certainty.

In accordance with the invention, the abutment or end location 23 is sized to provide that the source is supported in its correct position for opening of its valve on operation of the cam mechanism 8.

Figure 3:
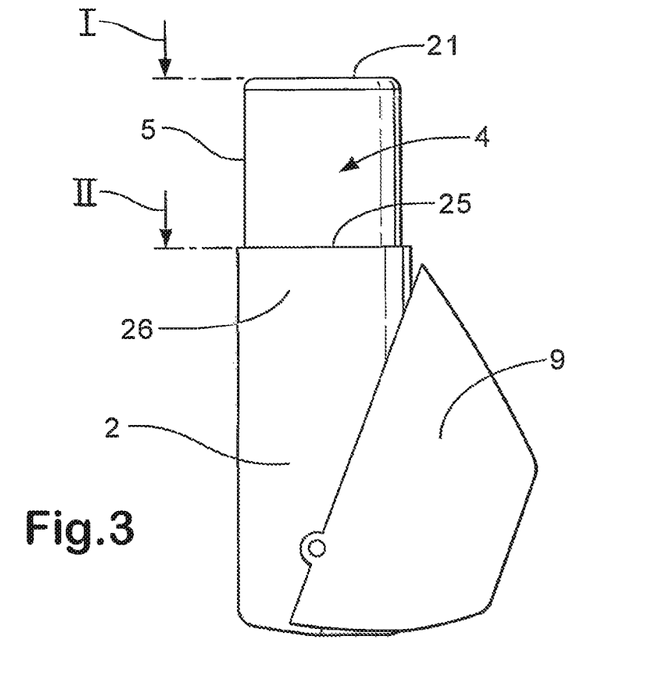
FIG. 3 is a plain side view corresponding to FIG. 1, without a closed sleeve fitted to the body of the dispenser and showing measurement of the length of the source.
Figure 4:
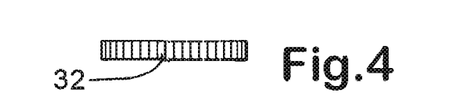
FIG. 4 is a side view of an adjustable, abutment location prior to compression to length.

This sizing is a two stage operation: 1. The dimension from the end 21 of the source to the end surface 25 of the source receptacle 26 is measured. This measurement is shown in FIG. 3 by the arrows I and II, indicating two actual measurements from a datum with the desired measurement being the difference of the actual measurements. This measurement operation can be performed in any conventional manner known to the man skilled in the art and is likely to be performed optically on a production line.

Figure 5:
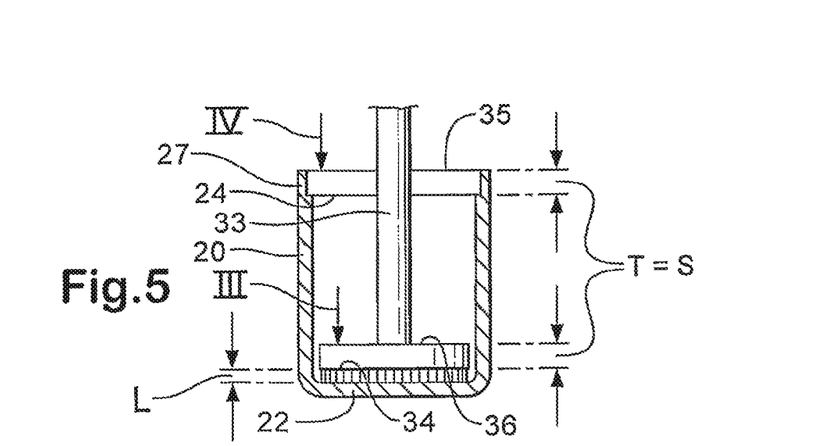
FIG. 5 is a cross-sectional side view of the closed sleeve with its location being compressed to a thickness to suit the length of the source.
Figure 6:
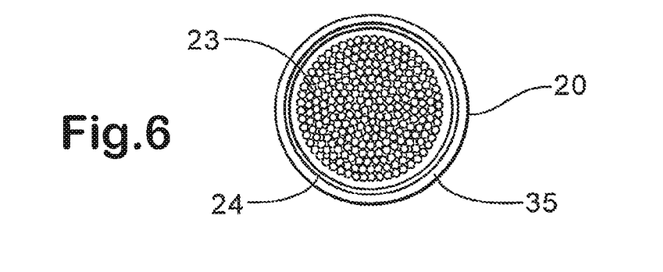
FIG. 6 is an end view of the closed sleeve showing the compressed location.

2. With knowledge of the effective length of the source, the actual length being predictable as the effective length plus the distance below the surface 25 at which the end of the spout is located, the required length of the end location 23 can be calculated, taking account of length of the closed sleeve. As shown in FIG. 5 the abutment is compressed to the required length. The end location itself is a disc 32 of aluminium honeycomb of a wall thickness that can be readily compressed to the required dimension, yet can resist the force exerted on it in operation, when the canister is urged against it. It should be noted that the compression is plastic and permanent. The compression is carried out with the disc in situ in the closed sleeve against the end surface 25 and by means of a plunger 33. Conveniently the plunger is the same thickness as the depth of the skirt step 27, whereby the effective depth of the closed sleeve from the compressed surface abutment face 34 of the disc to the step 24 is the same as the dimension top of the plunger to the end 35 of the skirt.

Figure 7:
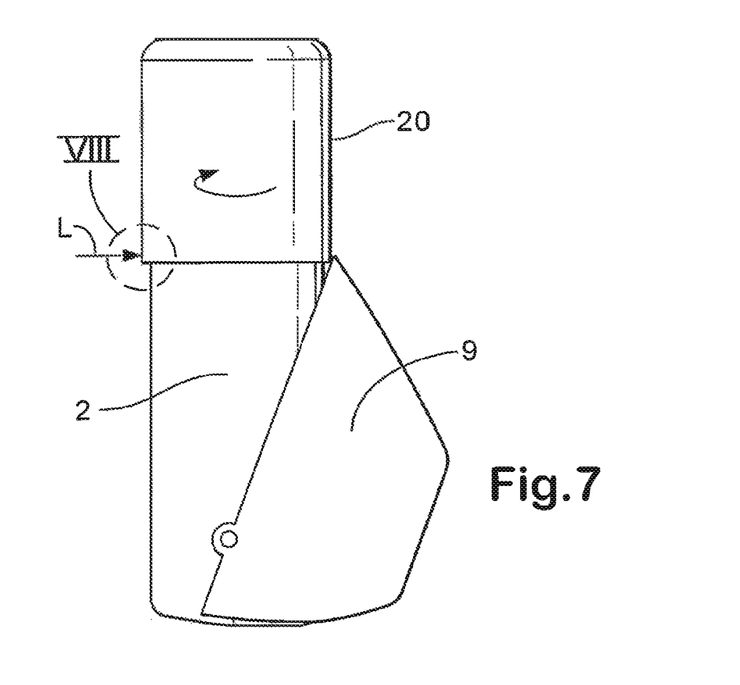
FIG. 7 is a view similar to FIG. 3, showing the closed sleeve being welded to the body.
Figure 8:
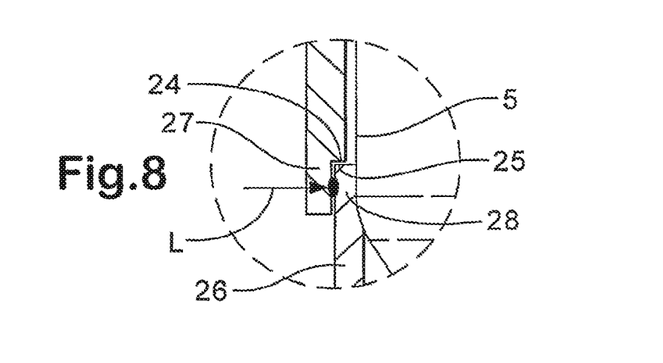
FIG. 8 is a scrap cross-sectional view of the encircled VIII portion of FIG. 7.

After sizing of the abutment, the closed sleeve is assembled to the body over the source, with the step abutting the end surface of the body. The skirt is then laser welded to the body. The result is that the source is supported firmly for displacement of the spout inwards on operation of the cam mechanism by opening of the cover.

To avoid any possibility of the source being permanently under slight compression, the abutment may be compressed by a small amount extra to allow a small, but defined lost motion on initial movement of the cam.

Figure 9:
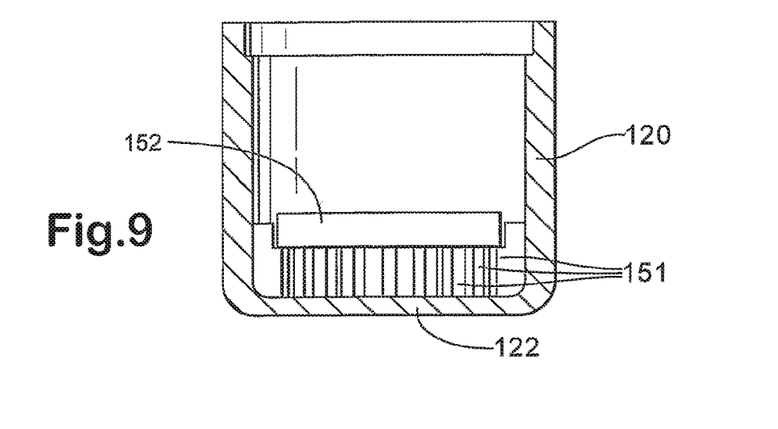
FIG. 9 is a view similar to FIG. 5 of an alternative location.

Referring now to FIG. 9, an alternative abutment is shown in a sleeve 120 analogous to the sleeve 20. It is of injection moulded plastics material. At the inside of its end 122, it is provided with many thin, radial ribs 151, arranged around the radially outer part of the inside of the end 122. The ribs are plastically deformable. They can be compressed and form an abutment or adjusted location directly themselves for the source. Alternatively, a solid disc 152, of metal or plastics material can be used to provide an actual abutment or location surface for the end of the source.

Figure 10:
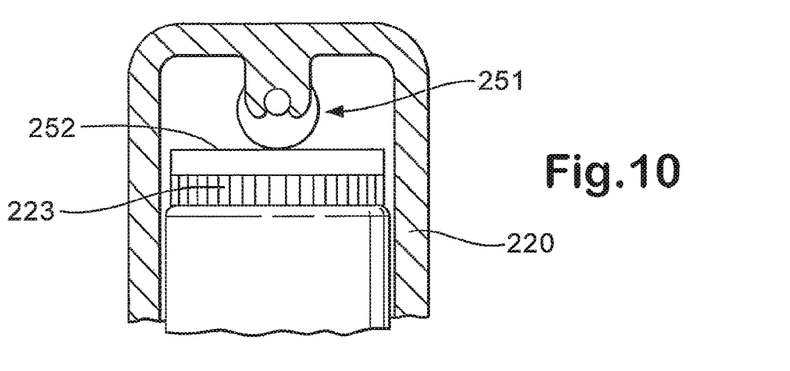
FIG. 10 is a diagrammatic view of a dispense-mechanism housed in a source sleeve and an adjusted location of the invention.
Figure 11:
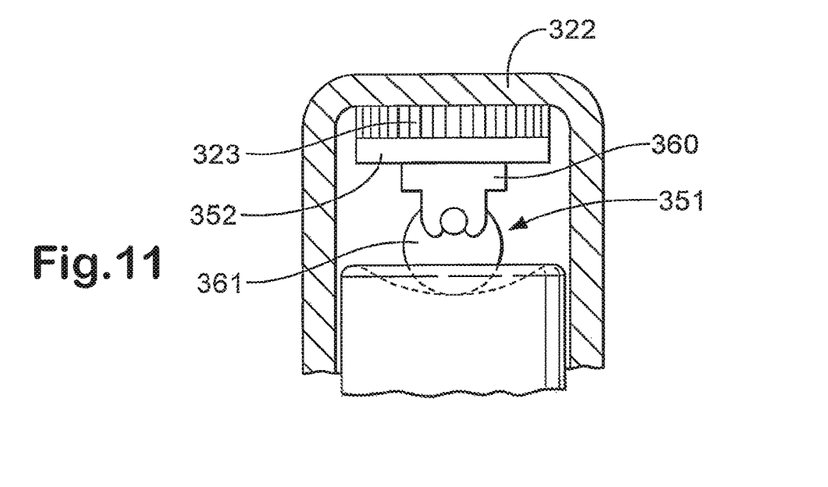
FIG. 11 is a view similar to FIG. 10 of another similar dispense-mechanism and an adjusted location of the invention.

Each of FIGS. 10 and 11 show diagrammatically a cam-driven source-movement mechanism 251,351, respectively above and below a honeycomb compressible abutment 223, 323 having a reinforcement disc 252,352. In FIG. 10, the mechanism is coupled to the sleeve 220 and acts on the disc 252 to drive the source towards the junction member (not shown) in the dispenser, the junction member being fixed with respect to the sleeve and the body of the dispenser in this instance. The abutment is sized in like manner to the abutment 23, as described above. In FIG. 11, the abutment 323 acts directly against the inside of the end 322 of the container, with a fixed part 360 of the mechanism acting on the reinforcement disc 352. A movable part 361, a cam as drawn, acts directly on the source.

Figure 12:
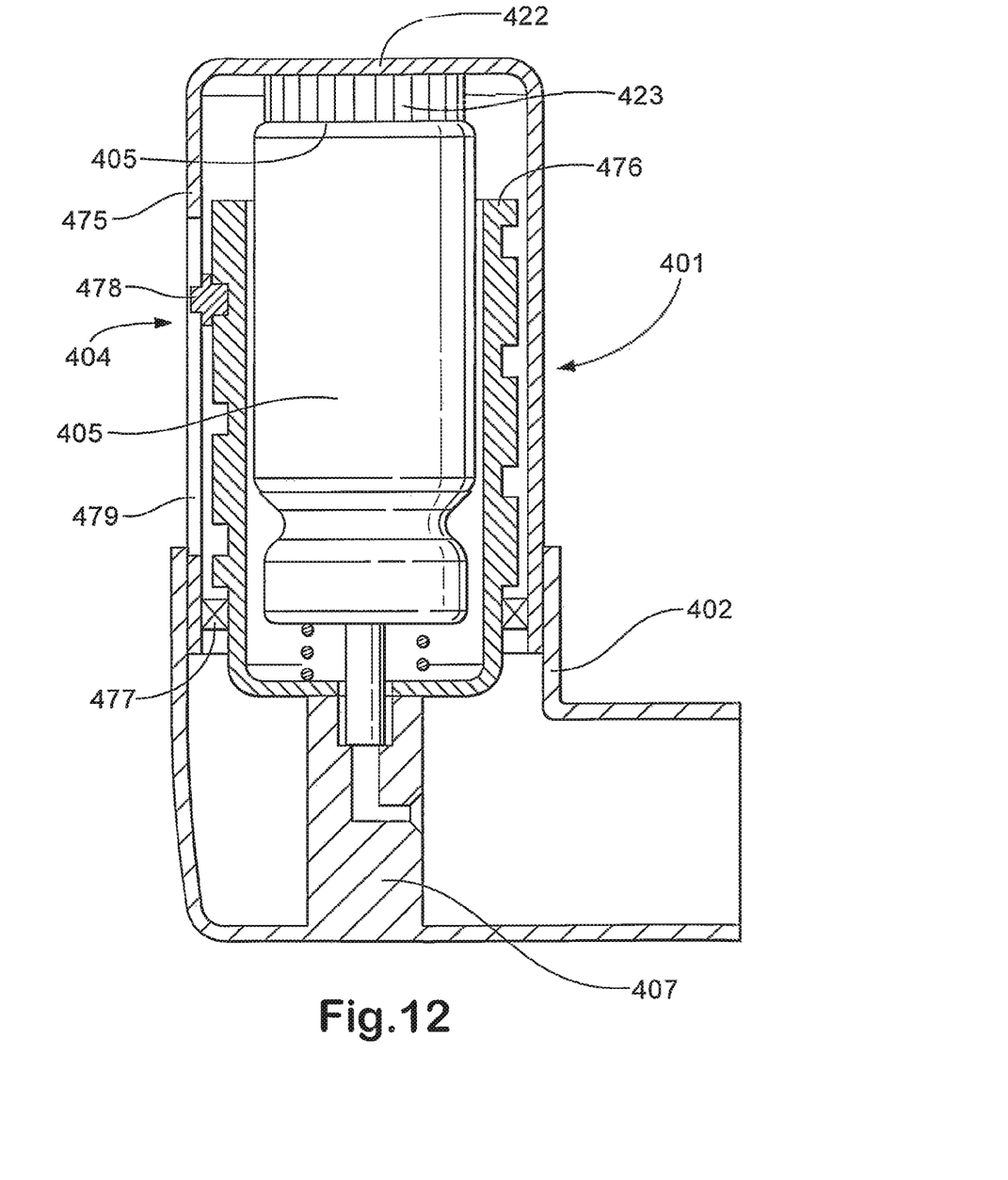
FIG. 12 is a cross-sectional side view of another dispenser utilising the invention.

Turning on to FIG. 12, a dispenser 401 which is not breath actuated, is shown. It has a junction member 407 fixed in its body 402. Its source 404 includes a canister 405 and a pair of concentric sleeves 475,476, which are arranged with a ratchet mechanism 477 to drive an indicator 478 along a slot 479 in the outer sleeve to indicate the number of doses dispensed and remaining to be dispensed. The ratchet mechanism is an intricate device and its reliable operation can be adversely affected by the loose tolerances to which the source is assembled. A location member 423, sized in a manner analogous to that in the above embodiments, is provided between the canister 405 and the end 422 of the outer sleeve 475. Sizing of the location provides that the complementary parts of the mechanism inter-engage correctly for their reliable operation.

It should be noted that for the purposes of the present invention, this counter for counting the number of doses is included in the term "dispense-mechanism", namely a mechanism in a dispenser which is operated on dispensing of a dose.

Figure 13:
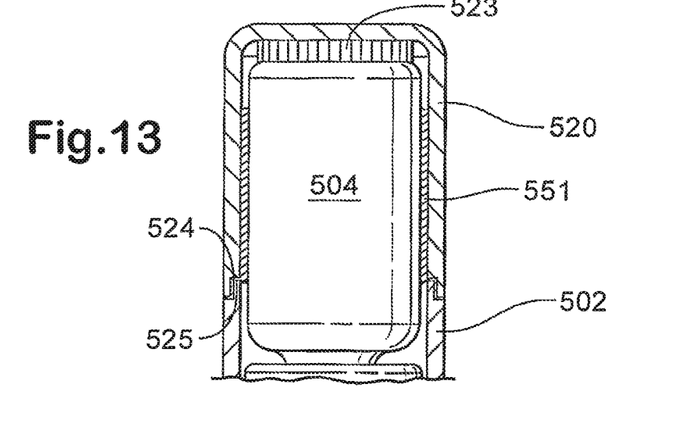
FIG. 13 is a scrap cross-sectional view of another adjusted location of the invention.

Turning now to the dispenser shown in FIG. 13, it has substantial similarity with that of FIG. 1, and its source end only is shown in cross-section. Its adjustable location 523 is reinforced in its positioning of its source 504, by adhesive 551 provided between sleeve 520 and the canister. Use of the adhesive provides that should the spring of the valve within the source be outside tolerance, there is a reserve of location strength and the crushable location is not unintentionally crushed further. The adhesive 551 can be applied in such a way as to fasten the sleeve 520 to the body 502 in addition to fastening the source in the sleeve at the positioning features 524,525.

Figure 14:
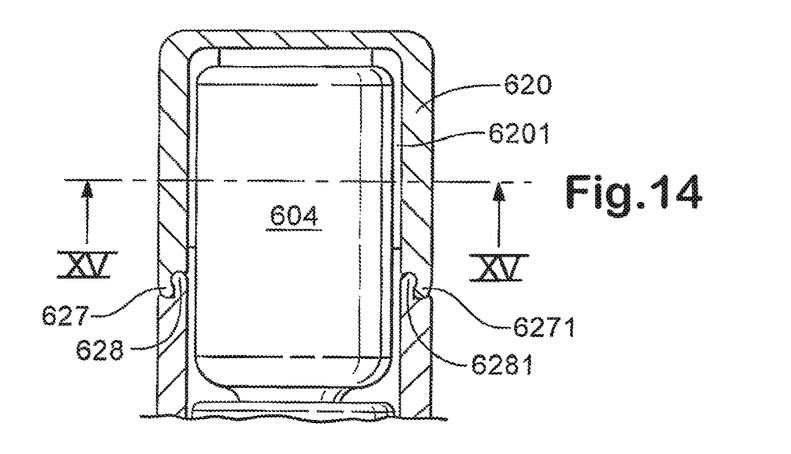
FIG. 14 is a further scrap cross-sectional view of an adjusted location of the invention.
Figure 15:
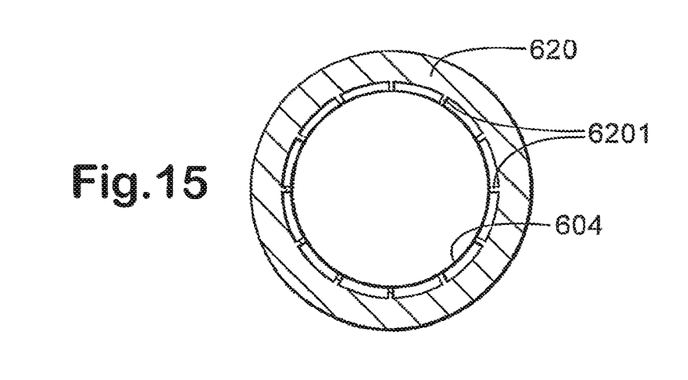
FIG. 15 is a cross-sectional view through the sleeve and source, shown in the line XV-XV in FIG. 14.

Turning on again to FIGS. 14 and 15, the sleeve 620 has internal ribs 6201 along its length, which are an interference fit with the source 604. The skirt 627 and the end portion 628 of the body 602 have respective complementary formations 6271,6281, which inter-engage when the sleeve is fitted to the body. The source is pushed into the sleeve to provide the desired dimension between the end of the sleeve and end of the spout. The fit is such is as to hold the source in its use position. This embodiment has the advantage of using entirely mechanical location of the source and connection of the sleeve to the body.

More generally, it should be noted that, the tolerance in the size of the body, the enclosure sleeve, the junction and the other parts of the dose dispense-mechanism, being injection moulded members, are considerably tighter than those of the source, whose valve includes elastomeric members held together with a metallic crimp. Accordingly, measurement of the length of the source and adjusting the abutment to this length and the nominal size of the moulded members can provide support of the source for reliable operation. The length of the source can be measured indirectly by measuring the position of the end of the source with respect to a datum in the body, with the source and the spout held towards the junction member with no slack. The location can then be adjusted to provide a determined position of the source when supported in comparison with another datum on the sleeve.

Whilst it is possible for the measurement to be made with the dose dispense-mechanism in its state for moving the spout for release of a dose from the source and the source urged towards the junction for such release and the adjustment being compensated for stroke of the junction member and the spout; in the above embodiments, the measurement is made with the spout in its quiescent position with respect to the source and the junction member and the release mechanism being in their normal rest position state from which they are moved for dose release.

It is envisaged that the abutment may be adjusted by machining, however in the preferred embodiments using a crushed location, crushing is with a force controlled to be a determined amount higher than the dose release force of the source, i.e. the force required to overcome the aerosol valve spring. Typically, where the release force is 40 N, the crush force is approximately 80 N or more.

The invention claimed is:

1. An enclosed aerosol source combination comprising an assembled combination of the aerosol source, a body and an enclosure:
   the aerosol source having:
      a canister,
      a spout at one end of the canister, the spout being movable inwards of the canister for substance release,
      a spring urging the spout outwards of the canister with a force required to be overcome for release movement inwards, and
      a valve for releasing a substance from the canister on longitudinal movement of the spout against the spring;
   the body having:
      a mouthpiece for inhalation/insufflation of the substance;

a moveable junction member for receiving the spout; and a dispense mechanism able to be cocked to move the junction member and receive a substance dose and to be triggered by inhalation releasing the substance dose;

the enclosure having:

at least one dispense-mechanism positioning feature at a determined position; and a location member for the canister, the location member configured to be adjusted to provide a determined dose of the spout with respect to the at least one dispense-mechanism positioning feature after the aerosol canister has been assembled into the enclosure, an arrangement of the assembled combination being such that on movement of the spout through determined stroke with respect to the dispense-mechanism, positioning feature and against the spring substance release is predictable.

2. The enclosed aerosol source combination as claimed in claim 1, wherein the at least one dispense-mechanism positioning feature is an enclosure abutment feature for the body included in the combination, the body having:

a second abutment feature for abutment of the enclosure abutment feature; the two abutment features being connected together by a connection means.

3. The enclosed aerosol source combination as claimed in claim 2, wherein the connection means of the two abutment features are selected from the group consisting of interengagement of complementary features, a welded joint and an adhesive joint.

4. The enclosed aerosol source combination as claimed in claim 1, wherein the location member is a compressed end location member for the canister in the enclosure.

5. The enclosed aerosol source combination as claimed in claim 4, wherein the location member is a part added to the enclosure.

6. The enclosed aerosol source combination as claimed in claim 5, wherein the location member is a washer of aluminium honeycomb material.

7. The enclosed aerosol source combination as claimed in claim 4, wherein the location member is a deformable part of the enclosure.

8. The enclosed aerosol source combination as claimed in claim 7, wherein the location member is an integrally moulded honeycomb or set of radial ribs.

9. The enclosed aerosol source combination as claimed in claim 7, wherein the location member includes a rigid disc or washer pressed into the deformable part of the enclosure.

10. The enclosed aerosol source combination as claimed in claim 1, wherein the enclosure is imperforate at the end of the canister opposite from the spout and along a side thereof.

11. The enclosed aerosol source combination as claimed in claim 1, wherein the enclosure is skeletal.

12. An adjustment method of the enclosed aerosol source as claimed in claim 1, the method consisting in the steps of:

measuring the overall length of the source from the distal end of the source's spout to the source's other end;

adjusting the location member for the canister; and assembling the aerosol source, the body and the enclosure to form the enclosed aerosol source combination.

13. The adjustment method as claimed in claim 12, wherein the location member is a compressed end location member for the canister in the enclosure, and wherein:

the adjusting consists of compressing the location member to a standard dimension less the overall length of the source, the standard dimension being the distance from a support for the location member and the at least one dispense-mechanism positioning feature and a fixed use dimension from the at least one dispense-mechanism positioning feature to the distal end of the spout.

14. The adjustment method as claimed in claim 12, wherein the location member is adjusted by machining.

15. The adjustment method as claimed in claim 12, wherein the adjustable location is adjusted by crushing with a force controlled to be a determined amount higher than the dose release force of the source.

16. The adjustment method as claimed in claim 15, wherein the crush force is substantially double the release force.

17. The adjustment method as claimed in claim 12, wherein the location member is adjusted by plastic deformation of the location member.

18. An adjustment method utilising the enclosed aerosol source combination as claimed in claim 1, comprising the steps of:

measuring the overall length of the source from the distal end of the source's spout to the source's other end, wherein the measuring consists of indirectly measuring the overall length of the source by measuring a position of an end of the source with respect to a datum in the body, with the source and the spout held towards the junction member with no end float; and adjusting the location member so as to provide a determined position of the spout with respect to the at least one dispense-mechanism positioning feature.

19. The adjustment method as claimed in claim 18, wherein the measuring is carried out with the dose release mechanism in a state for moving the spout for release of a dose from the source and the source urged towards the junction member for such release and the adjustment being compensated for stroke of the junction member and the spout.

20. The adjustment method as claimed in claim 18, wherein the measuring step is made with the spout in a quiescent position with respect to the source and with the junction member and the dose release mechanism being in their normal rest position state from which they are moved for dose release.

21. The adjustment method as claimed in claim 18, wherein the adjustment of the location member is such that the canister is supported with negligible end float.

22. The enclosed aerosol source combination as claimed in claim 1, wherein the body is devoid of any feature intended for longitudinal location of the canister.

* * * * *